US008828969B2

(12) United States Patent
Hosokawa et al.

(10) Patent No.: US 8,828,969 B2
(45) Date of Patent: Sep. 9, 2014

(54) PHARMACEUTICAL COMPOSITION FOR RELIEVING PAIN

(75) Inventors: Hiroyuki Hosokawa, Tokyo (JP); Sooyeol Lim, Tokyo (JP); Junko Oda, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 132 days.

(21) Appl. No.: 13/390,261

(22) PCT Filed: Aug. 13, 2010

(86) PCT No.: PCT/JP2010/005060
§ 371 (c)(1),
(2), (4) Date: Feb. 13, 2012

(87) PCT Pub. No.: WO2011/018902
PCT Pub. Date: Feb. 17, 2011

(65) Prior Publication Data
US 2012/0142629 A1 Jun. 7, 2012

(30) Foreign Application Priority Data
Aug. 13, 2009 (JP) ................................ 2009-187899

(51) Int. Cl.
*A61K 31/738* (2006.01)
*A61P 29/00* (2006.01)
*A61K 31/728* (2006.01)
*A61K 9/00* (2006.01)
*C08B 37/08* (2006.01)

(52) U.S. Cl.
CPC ............. *A61K 31/728* (2013.01); *A61K 31/738* (2013.01); *A61K 9/0024* (2013.01)
USPC ....................................................... 514/54

(58) Field of Classification Search
None
See application file for complete search history.

(56) References Cited

U.S. PATENT DOCUMENTS

| 5,356,883 | A | 10/1994 | Kuo et al. |
| 5,763,504 | A | 6/1998 | Matsuda et al. |
| 6,031,017 | A | 2/2000 | Waki et al. |
| 6,107,410 | A | 8/2000 | Waki et al. |
| 6,602,859 | B2 | 8/2003 | Miyamoto et al. |
| 7,931,030 | B2 | 4/2011 | Bailleul |
| 2006/0148755 | A1 | 7/2006 | Bailleul |
| 2011/0053885 | A1 | 3/2011 | Miyamoto et al. |

FOREIGN PATENT DOCUMENTS

| EP | 0718312 A2 | 6/1996 |
| EP | 0939086 A1 | 9/1999 |
| EP | 1 905 456 A1 | 4/2008 |
| JP | 06-073102 A | 3/1994 |
| JP | 08143604 A | 6/1996 |
| JP | 11512778 | 11/1999 |
| JP | 2002249501 A | 9/2002 |
| WO | WO-0157093 A1 | 8/2001 |
| WO | WO-2007004675 A1 | 1/2007 |
| WO | 2008069348 A1 | 6/2008 |

OTHER PUBLICATIONS

Raman, R. et al "Efficacy of Hylan G-F 20 and sodium hyaluronate . . . " The Knee (2008) vol. 15, pp. 318-324.*
Supplementary Search Report dated Jan. 8, 2013.
International Preliminary Report on Patentability (IPRP) dated Mar. 23, 2012.
Seikagaku Corporation Annual Report 2006, Jan. 1, 2007, pp. 1-3, XP002689774.
Barak H S et atl: "326: Effectiveness and safety of a single intraarticular injection of gel-200, a new cross-linked formulation of hyaluronic acid [HA] in the treatment of symptomatic osteoarthritis [OA] of the knee". Osteroarthritis and cartilage, bailliere tindall, London, GB, vol. 17 Sep. 1, 2009, p. S174, XP026582210.
Barah H S et al: "341 Duration of a single interaarticular injection of gel-200 and safety of re-treatemnt of gel-200, a new cross-liked formulation of hyaluronic acid [HA] in the treatment of symptomatic osteoarthritis [OA] of the knee", Osteroarthritis and cartilage, bailliere tindal, London, GB vol. 17, Sep. 1, 2009, p. S181, XP026582225.
Barbucci, et al., "Hyaluronic Acid Hydrogel in the Treatment of Osteoarthritis", Biomaterials, vol. 23, pp. 4503-4513 (2002), 11 pages, Elsevier Science Ltd.
Cattell, J., "Written Opinion of the International Searching Authority", International Application No. PCT/JP2007/073987, mailed Jun. 6, 2009, 5 pages, Patent Cooperation Treaty, European Patent Office, Munich, Germany.

(Continued)

*Primary Examiner* — Leigh Maier
(74) *Attorney, Agent, or Firm* — Edwards Wildman Palmer LLP; Peter F. Corless; Christopher R. Cowles

(57) ABSTRACT

The present invention relates to a pharmaceutical composition for relieving pain in a joint disease, including a hyaluronic acid and a pharmaceutically acceptable carrier, in which the hyaluronic acid is cross-linked by cyclizing a double bond in the moiety of a cinnamic acid in a partially amidated hyaluronic acid represented by Formula (1):

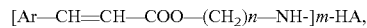

[Ar—CH=CH—COO—(CH$_2$)$n$—NH-]$m$-HA, to form a cycloubutane ring, in which Ar represents an optionally substituted phenyl group, n represents an integer of 2 or 3, HA represents a carboxy residue of the hyaluronic acid, and m represents an amidation ratio of the hyaluronic acid to the total carboxyl group and is in the range of 3 to 50% relative to the total carboxyl group.

The pharmaceutical composition of the present invention is an intra-articular formulation that exerts rapid analgesic effects after administration, and shows extremely long durable effects for a human joint disease with only a single administration rather than multiple administrations of a conventional way.

6 Claims, 1 Drawing Sheet

(56) References Cited

OTHER PUBLICATIONS

Honda, et al., "Notification Concerning Transmittal International Preliminary Report on Patentability", Patent Cooperation Treaty, International Application No. PCT/JP2007/073987, mailed Jun. 18, 2009, 6 pages, The International Bureau of the WIPO, Geneva, Switzerland.

Maier, L. C., Office Action Dated Oct. 28, 2011, U.S. Appl. No. 12/448,064, mailed Oct. 28, 2011, 10 pages, United States Patent and Trademark Office, Alexandria, VA.

Miyamoto, et al., "Evaluation of in vivo Biocompatibility and Biodegradation of Photocrosslinked Hyaluronate hydrogels (HADgels)", J. Biomed. Mater. Res., vol. A70, pp. 550-559, Jul. 2004.

Office Action dated Dec. 13, 2010, The State Intellectual Property Office of the People's Republic of China, Application No. 200780045074.5, Document No. 2010120800158810, 13 pages.

"Start of a Clinical Trial in the United States of Cross-Linked Hyaluronate Hydrogel", Seikagaku Corporation, Jul. 2006, 3 pages, Chiyoda-ku, Tokyo.

Day et al., "A Double Blind, Randomized, Multicenter, Parallel Group Study of the Effectiveness and Tolerance of Intraarticular Hyaluronan in Osteoarthritis of the Knee", The Journal of Rheumatology, vol. 31, No. 4, pp. 775-782 (2004).

Altman et al., "Efficacy and safety of a single intra-articular injection of non-animal stabilized hyaluronic acid (NASHA) in patients with osteoarthritis of the knee", OsteoArthritis and Cartilage, vol. 12, No. 8, pp. 642-649 (2004).

Dixon et al., "Clinical trial of intra-articular injection of sodium hyaluronate in patients with osteoarthritis of the knee", Current Medical Research and Opinion, vol. 11, No. 4, pp. 205-213 (1988).

Chevalier et al., "Sings, intra-articular treatment with 6 mL of hylan G-F 20 in patients with symptomatic primary osteoarthritis of the knee: A randomised, multi-centre, double-blind, placebo-controlled trial", Annals of the Rheumatic Diseases, pp. 1-14 (2009).

Altman et al., "Recommendations for the Medical Management of Osteoarthritis of the Hip and Knee", Arthritis & Rheumatism, vol. 43, No. 9, pp. 1905-1915 (2000).

* cited by examiner

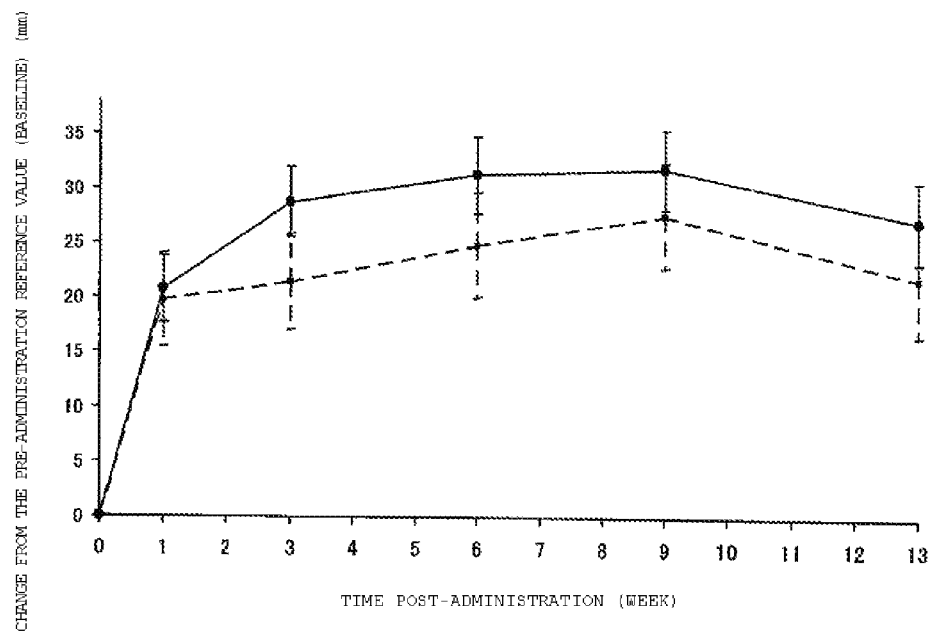

PHARMACEUTICAL COMPOSITION FOR RELIEVING PAIN

CROSS-REFERENCES TO RELATED APPLICATIONS

This application is a 35 U.S.C. §371 U.S. national entry of International Application PCT/JP2010/005060 (WO 2011/018902) having an International filing date of Aug. 13, 2010, which claims under 35 U.S.C. §119(a) the benefit of Japanese Application No. 2009-187899, filed Aug. 13, 2009, the entire contents of which are incorporated herein by reference.

TECHNICAL FIELD

The invention relates to a pharmaceutical composition for relieving pain in joint disease including a cross-linked hyaluronic acid and a pharmaceutically acceptable carrier.

BACKGROUND ART

In the aging modern society, osteoarthritis (hereinafter, referred to as OA), which is joint pain and functional disorder attributable to joint degeneration, is the most common joint disease throughout the world, and is one of the leading causes of disability in daily life of the elderly.

Currently, OA treatments include, for example, a treatment by oral administration of analgesic drug such as non-steroidal anti-inflammatory drug, which is broadly used for various pains, and a treatment by intra-articular administration of hyaluronic acid solution.

The former treatment is a symptomatic therapy for relieving joint pain with use of a synthetic medicine having sharp analgesic effects.

On the other hand, the latter treatment is a therapy for treating joint disease, which is impaired joint function attributable to reduction of the joint fluid and degeneration of joint cartilage, by lubricant action, shock absorber action, cartilage metabolism improvement action and joint pain relieving action, which are possessed by the hyaluronic acid.

Hereinafter, hyaluronic acid or a derivative group therefrom may be referred to as HA.

Currently, intra-articular formulations using hyaluronic acid and derivative thereof (hereinafter, referred to as the IA-HA product.) are commercially available as products formed from solution of sodium hyaluronate, and products formed from solution of a cross-linked hyaluronic acid derivative. Examples of the IA-HA products formed from solution of sodium hyaluronate include ARTZ (registered trademark), SYNVISC (registered trademark), HYALGAN (registered trademark), and ORTHOVISC (registered trademark). Examples of the IA-HA product formed from solution of a cross-linked hyaluronic acid derivative include SYNVISC (registered trademark) and DUROLANE (registered trademark). SYNVISC (registered trademark) is composed of a hyaluronic acid derivative cross-linked with a covalent bond by a small amount of aldehyde, and a hyaluronic acid derivative made by further cross-linking the derivative by divinyl sulfone. DUROLANE (registered trademark) is an epoxy cross-linked joint protective agent (see U.S. Patent Application Publication No. 2006/0148755).

These IA-HA products are administered basically every 1 to 2 weeks to obtain desired therapeutic effects (see "The Journal of Rheumatology" 2004, 31: 4, pp. 775-782; and "Current Medical Research and Opinion" 11: 205-213, 1988). Since hyaluronic acid has viscoelasticity, intra-articular administration of these IA-HA products is performed with use of a thicker injection needle than that for usual injections. Therefore, the intra-articular administration of these IA-HA products gives the feels of more invasion and boring pain than administration of usual injections, and the administration of these IA-HA products in the single treatment period is limited to 5 times in principle in Japan. However, conventional products require continuous administrations every week, which may become a great burden to patients who reside at a distant place from the hospital or who have difficulty in visiting weekly owing to the job of the patients. Accordingly, products requiring administrations at fewer frequencies and showing equivalent or better therapeutic effects to or than those of the conventional IA-HA products are sought.

Recently, there has been reported a product (SYNVISC-ONE (trademark)) that is a new regimen using SYNVISC (registered trademark) and allows a single injection with increased dosage up to three times a usual dosage (2 mL) of conventional products. According to the report, it is believed such that the therapeutic effects last for 26 weeks after a single administration (see "ARD Online First," published on Mar. 19, 2009 as 10. 1136/ard. 2008. 094623). However, such therapeutic effects are only results from the single administration with three-time dose (6 mL) of the conventional product. Further, there is also a demerit that a burden to patients is increased by triple dose intra-articular injection at one shot compared to the conventional product.

In addition, International Publication Pamphlet No. WO 2008/069348 reports a therapeutic agent for a joint disease for intra-articular administration by a photo cross-linked hyaluronic acid derivative, which is a different cross-linked form from that of the commercially available cross-linked hyaluronic acids, and has durable effects with a single administration. However, there is no specific disclosure or suggestion regarding the ultralong-term durability in human OA treatment.

In addition, IA-HA products are focused on long term enhancement of patient's QOL by improving comprehensive joint functions, and hardly expected to have rapid-acting analgesic effects as expected in, for example, non-steroidal anti-inflammatory analgesic drugs (see "The Journal of Rheumatology" 2004, 31: 4, pp. 775-782; "OsteoArthritis and Cartilage" (2004) 12, 642-649; "ARD Online First," published on Mar. 19, 2009 as 10. 1136/ard. 2008. 094623; "Arthritis & Rheumatism," Vol. 43, No. 9, pp. 1905-1915 (2000)).

As described above, a number of IA-HA products exist, but there has been no report of an intra-articular formulation that shows equivalent or better effects with a single administration to or than the effects shown with multiple administrations of any of conventional IA-HA products, without an increase of the single dosage, and for a long period, particularly more than a half year from the viewpoint of invasion.

Consequently, desired are products that can have early onset of prominent analgesic effects, with a lower frequency of administration and a smaller dosage of a single administration as possible, and show equivalent or better therapeutic effects to or than conventional IA-HA products.

SUMMARY OF THE INVENTION

Problems to be Solved by the Invention

An object of the present invention is to provide an intra-articular formulation that exerts rapid analgesic effects after administration, and shows extremely long durable effects for human joint disease with only a single administration rather than multiple administrations, in which a dosage of the single administration is substantially no change from the dosage of the single administration of the conventional IA-HA products which are served with multiple administrations, and the like.

Means for Solving the Problems

The inventors of the present invention have studied earnestly to solve the above problems, and as results, found that when a cross-linked hyaluronic acid having short-chain amino alcohol as a spacer is used, it shows early pain alleviation effects whereas conventional IA-HA products show no such early pain alleviation effects. In addition, the inventors have found that such product shows extremely long durable effects, for example, over a half year for a human joint disease with only a single administration of a dosage that is nearly no change from the single dosage of the conventional IA-HA products that are served with multiple administrations, whereby to complete the invention.

According to one aspect of the present invention, there is provided a pharmaceutical composition for relieving pain in a joint disease, including a hyaluronic acid and a pharmaceutically acceptable carrier, in which the hyaluronic acid is cross-lined by cyclizing a double bond in a moiety of a cinnamic acid in a partially amidated hyaluronic acid represented by Formula (1):

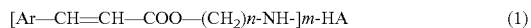

[Ar—CH=CH—COO—(CH₂)n-NH-]m-HA  (1)

to form a cyclobutane ring, in which Ar represents an optionally substituted phenyl group, n represents an integer of 2 or 3, HA represents a carboxy residue of a hyaluronic acid, and m represents an amidation ratio of the hyaluronic acid to the total carboxyl group and represents 3 to 50% relative to the total carboxyl group.

The content of the cross-linked hyaluronic acid in this pharmaceutical composition is preferably 0.5 to 3.0% by weight per volume relative to the total product.

In addition, this pharmaceutical composition is desirably in a single-dose preparation. In this case, this pharmaceutical composition is preferably administered at an administration interval of 13 weeks or more.

In addition, this pharmaceutical composition is preferably used for durable effects up to at least 13 weeks, more preferably for durable effects up to at least 26 weeks.

The present invention will be more specifically described below.

(1) A pharmaceutical composition for relieving pain in a joint disease, including a hyaluronic acid and a pharmaceutically acceptable carrier, the hyaluronic acid being cross-linked by cyclizing a double bond in a moiety of a cinnamic acid in a partially amidated hyaluronic acid represented by Formula (1):

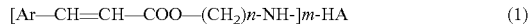

[Ar—CH=CH—COO—(CH₂)n-NH-]m-HA  (1)

(in which Ar represents an optionally substituted phenyl group, n represents an integer of 2 or 3, HA represents a carboxy residue of a hyaluronic acid, and m represents an amidation ratio of a hyaluronic acid to the total carboxyl group and represents 3 to 50% relative to the total carboxyl group), to form a cyclobutane ring.

(2) The pharmaceutical composition as described in the above (1), wherein a ratio (a degree of cross-linking) of the double bond in a moiety of a cinnamic acid which forms a cyclobutane ring by cyclizing is 5 to 40%.

(3) The pharmaceutical composition as described in the above (1) or (2), wherein the content of the cross-linked hyaluronic acid is 0.5 to 3.0% by weight per volume of the total product.

(4) The pharmaceutical composition as described in any one of the above (1) to (3), wherein the pharmaceutical composition is an injection product.

(5) The pharmaceutical composition as described in the above (4), wherein a single dosage of the injection product is 2 to 3 mL.

(6) The pharmaceutical composition as described in any one of the above (1) to (5), wherein the pharmaceutical composition is a single-dose preparation.

(7) The pharmaceutical composition as described in the above (6), wherein the single-dose preparation is administered at an administration interval of 13 weeks or more.

(8) The pharmaceutical composition as described in any one of the above (1) to (7), wherein the pharmaceutical composition is used for durable effects up to at least 13 weeks.

(9) The pharmaceutical composition as described in the above (8), wherein the pharmaceutical composition is used for durable effects up to at least 26 weeks.

(10) A hyaluronic acid cross-linked by cyclizing a double bond in a moiety of a cinnamic acid in a partially amidated hyaluronic acid represented by Formula (1):

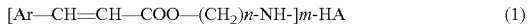

[Ar—CH=CH—COO—(CH₂)n-NH-]m-HA  (1)

(in which Ar represents an optionally substituted phenyl group, n represents an integer of 2 or 3, HA represents a carboxy residue of a hyaluronic acid, and m represents an amidation ratio of a hyaluronic acid to the total carboxyl group and represents 3 to 50% relative to the total carboxyl group), to form a cyclobutane ring, for use as a pharmaceutical composition for relieving pain in a joint disease.

(11) The hyaluronic acid as described in the above (10), wherein a ratio (a degree of cross-linking) of the double bond in a moiety of a cinnamic acid which forms a cyclobutane ring by cyclizing is 5 to 40%.

(12) The hyaluronic acid as described in the above (10) or (11), wherein the content of the cross-linked hyaluronic acid in the pharmaceutical composition is 0.5 to 3.0% by weight per volume of the total pharmaceutical composition.

(13) The hyaluronic acid as described in any one of the above (10) to (12), wherein the pharmaceutical composition is used as an injection product.

(14) The hyaluronic acid as described in the above (13), wherein a single dosage of the injection product is 2 to 3 mL.

(15) The hyaluronic acid as described in any one of the above (10) to (14), wherein the pharmaceutical composition is a single-dose preparation.

(16) The hyaluronic acid as described in the above (15), wherein the single-dose preparation is administered at an administration interval of 13 weeks or more.

(17) The hyaluronic acid as described in any one of the above (10) to (16), wherein the pharmaceutical composition is used for durable effects up to at least 13 weeks.

(18) The hyaluronic acid as described in the above (17), wherein the pharmaceutical composition is used for durable effects up to at least 26 weeks.

(19) A method for relieving pain of a patient in need of pain relief in a joint disease, including an administration of an effective dose of a hyaluronic acid and a pharmaceutical composition comprising pharmaceutically acceptable carrier, the hyaluronic acid being cross-linked by cyclizing a double bond in a moiety of a cinnamic acid in a partially amidated hyaluronic acid represented by Formula (1):

[Ar—CH=CH—COO—(CH₂)n-NH-]m-HA  (1)

(in which Ar represents an optionally substituted phenyl group, n represents an integer of 2 or 3, HA represents a carboxy residue of a hyaluronic acid, and m represents an amidation ratio of a hyaluronic acid to the total carboxyl group and represents 3 to 50% relative to the total carboxyl group), to form a cyclobutane ring, to a patient in need of pain relief in a joint disease.

(20) The method as described in the above (19), wherein a ratio (a degree of cross-linking) of the double bond in a moiety of a cinnamic acid which forms a cyclobutane ring by cyclizing is 5 to 40%.

(21) The method as described in the above (19), wherein the content of the cross-linked hyaluronic acid in the pharmaceutical composition is 0.5 to 3.0% by weight per volume of the total pharmaceutical composition.

(22) The method as described in the above (19), wherein the pharmaceutical composition is an injection product.

(23) The method as described in the above (22), wherein a single dosage of the injection product is 2 to 3 mL.

(24) The method as described in the above (19), wherein the pharmaceutical composition is a single-dose preparation.

(25) The method as described in the above (24), wherein the single-dose preparation is administered at an administration interval of 13 weeks or more.

(26) The method as described in the above (19), wherein the pharmaceutical composition is used for durable effects up to at least 13 weeks.

(27) The method as described in the above (19), wherein the pharmaceutical composition is used for durable effects up to at least 26 weeks.

Effects of the Invention

The present invention provides a hyaluronic acid product that has early onset of improvement effects for pain in joint disease. In addition, the present invention provides a single-dose preparation of which the dosage is substantially the same as that of the conventional one. The pharmaceutical composition of the invention shows rapid pain improvement effect after administration. Since this rapid effectiveness is not seen in the conventional IA-HA products, there is a potential that the active ingredient of the invention has different mechanisms from those of the conventional IA-HA products. In other words, it has been found for the first time in the invention that the cross-linked hyaluronic acid used in the invention has such potential.

In addition, the pharmaceutical composition of the invention shows extremely long durable effects for human joint disease simply with only a single administration of a dose that is nearly no change from the single dosage of conventional IA-HA products, which requires multiple administrations. The treatment is completed with a single administration without an increase of the injection burden to patients, and thus the risk of infections by microorganisms at the time of the injection decreases, and patients are also relieved from multiple boring pains. In addition, such effects are durable for an extremely long period, resulting in alleviation of burdens of the hospital visits and medical cost for patients. Furthermore, the administration interval may be extremely extended, so that it allows continuous treatments by the IA-HA products.

Furthermore, the pharmaceutical composition of the invention exhibits less side-effects, and is particularly preferable as a pharmaceutical composition.

BRIEF DESCRIPTION OF THE DRAWINGS

FIG. 1 is a diagram illustrating pain-relieving effects from 1 week to 13 weeks after the administration for the cross-linked hyaluronic acid derivative group and the PBS group. The horizontal axis represents weeks after the administration, and the vertical axis represents the difference (mm) between the pre-administration reference value (Baseline) and the VAS value at each week. The vertical lines on chart that extend up and down of the plot at 1, 3, 6, 9 and 13 weeks represent the standard deviation. The marks "●" represent the results of the cross-linked hyaluronic acid derivative group, and the marks "■" represent the results of the PBS group.

MODE FOR CARRYING OUT THE INVENTION

<1> Active ingredient

The active ingredient of the invention is a hyaluronic acid that is cross-linked by cyclizing a double bond in the moiety of a cinnamic acid in a partially amidated hyaluronic acid represented by the following Formula (1);

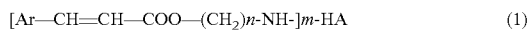

$$[Ar-CH=CH-COO-(CH_2)_n-NH-]_m-HA \qquad (1)$$

(wherein Ar represents an optionally substituted phenyl group, n represents an integer of 2 or 3, HA represents a carboxy residue of the hyaluronic acid, and m represents an amidation ratio of the hyaluronic acid to the total carboxyl group and represents 3 to 50% relative to the total carboxyl group), to form a cyclobutane ring. Hereinafter, this compound is referred to as the "cross-linked HA derivative."

The HA that composes this cross-linked HA derivative is not particularly limited as long as it has a disaccharide unit as a constituent unit, in which N-acetyl-D-glucosamine and D-glucuronic acids are bound to each other with a β1,3 bond, and it is glycosaminoglycan constituted by repetitive bonds of such disaccharide units by a β1,4 bond. In addition, the HA may be free from formation of a salt, or may form a pharmaceutically acceptable salt.

Examples of the pharmaceutically acceptable salts of the HA include alkali metal ion salts such as sodium salts and potassium salts, alkaline-earth metal ion salts such as magnesium salts and calcium salts, salts with an inorganic base such as ammonium salts, and salts with an organic base such as diethanolamine, cyclohexylamine, and an amino acid. More preferable example of the salt of the HA is alkali metal ion salts. Particularly preferable example is sodium ion salt.

The HA may be any of those which are derived from natural products obtained by extraction of a part of living organisms such as cock's comb, umbilical cord, cartilage and skin; those which are chemically synthesized; or those which are produced by culture or genetic engineering procedures using microorganisms such as yeast. Since the cross-linked HA derivative of the invention is administered to a living organism, the cross-linked HA derivative is preferably high-purity HA that contains nearly no substance, incorporation of which is not pharmaceutically acceptable.

The weight average molecular weight of the HA is not particularly limited, and is, for example, 10000 to 5000000. The weight average molecular weight of the HA is preferably 200000 to 3000000, and more preferably 500000 to 2500000.

In the cross-linked HA derivative, a substance in which a carboxyl group in such HA and a cinnamic acid aminoalkyl ester are amide-bounded to each other (hereinafter, referred to as the "photo-reactive HA derivative.") exists as a premise. Such substances are cross-linked with each other intermolecularly and/or intramolecularly by forming a cyclobutane ring in the moiety of the double bond of the cinnamic acid aminoalkyl ester residue.

In the Formula (1), the n represents the length of the alkylene moiety in the cinnamic acid aminoalkyl ester, and is preferably 2 or 3. In other words, the carbon is preferably present in the number of 2 or 3, and particularly has a linear structure. Examples thereof include an ethylene group or a trimethylene group. Examples of the cinnamic acid ester in the invention include a cinnamic acid 2-aminoethyl ester and a cinnamic acid 3-aminopropyl ester. A preferable example of the cinnamic acid ester is cinnamic acid 3-aminopropyl ester. In the description below, the cinnamic acid 3-aminopropyl ester is briefly referred to as cinnamic acid aminopropyl ester, and explanation will be given on such basis. It will be easily understood that cinnamic acid aminoethyl ester may be used instead of the cinnamic acid aminopropyl ester that will be explained below.

The photo-reactive HA derivative can be manufactured by allowing the amino group derived from aminopropanol, which composes the cinnamic acid aminopropyl ester, to bind to the carboxyl group of the HA by the amide-bond.

Such cinnamic acid aminopropyl ester is an ester compound in which the carboxyl group of a cinnamic acid and the hydroxyl group of 3-aminopropanol are bound to each other by the ester bond. This cinnamic acid aminopropyl ester may form a cyclobutane ring by allowing the vinylene groups to bind to each other, which are possessed by the cinnamic acid. The vinylene group possessed by the cinnamic acid has a property of causing photo dimerization reaction or photo polymerization reaction by light (ultraviolet) irradiation. Therefore, the cyclobutane ring is formed from two vinylene groups by light irradiation. In addition, the cinnamic acid that composes the cinnamic acid 3-aminopropyl ester may be a substituted cinnamic acid having a substituent.

Ar in the Formula (1) represents an optionally substituted phenyl. When Ar in the Formula (1) is a phenyl group having no substituent, the compound of the Formula (1) is a cinnamic acid ester. Meanwhile, when Ar is a phenyl group having a substituent, it is a substituted cinnamic acid ester. Examples of such substituent, which replaces any one or two hydrogens on the benzene ring of cinnamic, include a $C_{1-8}$ linear or branched lower alkyl group (for example, methyl, ethyl, propyl, isopropyl, butyl, t-butyl and the like), a $C_{1-8}$ linear or branched lower alkoxy group (for example, methoxy, ethoxy, propoxy, isopropoxy, butoxy and the like), an amino group optionally substituted with the alkyl group, a hydroxyl group, a halogen and the like.

All of the carboxyl groups in the HA in the photo-reactive HA derivative are not necessarily amide-bounded to the cinnamic acid aminopropyl ester, but only some of the carboxyl groups may be amide-bounded to the cinnamic acid aminopropyl ester.

The m in the Formula (1) represents a ratio (%) of the amide bond to the cinnamic acid aminoalkyl ester, to the total carboxyl group of HA. Hereinafter, the ratio m of the carboxyl group, which forms the amide bond, to the total carboxyl group present in HA is referred to as the "degree of substitution" (DS). The DS is calculated with the introduction ratio (%) of the cinnamic acid aminopropyl ester residue per disaccharide unit constituting HA. For example, the DS of the photo-reactive HA derivative to which one cinnamic acid aminopropyl ester residue is introduced per constituting disaccharide unit, or the DS of the photo-reactive HA derivative to which one cinnamic acid aminopropyl ester residue is introduced per constituting 200 saccharide units, are 100% and 1%, respectively.

The DS in the photo-reactive HA derivative in the invention, i.e., the ratio m is not particularly limited, but preferably 3% to 50%, more preferably 5% to 30%, and further more preferably 10% to 25%.

The cross-linked HA derivative used in the invention can be manufactured in accordance with methods described in the publications of Japanese Patent Application Laid-Open (JP-A) No. 2002-249501 and International Publication Pamphlet No. WO 2008/069348.

The manufacturing method is not particularly limited as long as it makes a cinnamic acid aminopropyl ester and HA chemically bind to each other by the amide bond. Examples of the method include a method of using a water-soluble condensation agent such as water-soluble carbodiimide (for example, 1-ethyl-3-(3-dimethylaminopropyl)carbodiimide hydrochloride (EDCI.HCl) and 1-cyclohexyl-3-(2-morpholinoethyl)carbodiimide-metho-p-tolu ene sulfonate; a method of using a condensing aid such as N-hydroxysuccinimide (HOSu) and N-hydroxybenzotriazole (HOBt) with the above condensation agent; a method of using a condensation agent such as 4-(4,6-dimethoxy-1,3,5-triazin-2-yl)-4-methylmorpholinium chloride (DMT-MM); an active esterification method; and an acid anhydride method.

The photo-reactive HA derivative may be prepared by making cinnamic acid and aminopropanol (for example, 3-aminopropanol, which is the same below) react to each other beforehand in order to prepare a cinnamic acid aminopropyl ester (for example, cinnamic acid 3-aminopropyl ester, which is the same below.), and subsequently making the amino group of the prepared cinnamic acid aminopropyl ester and the carboxyl group of the HA bind to each other by the amide bond. Alternatively, the photo-reactive HA derivative may be prepared by making the amino group of aminopropanol and the carboxyl group of HA to bind to each other by the amino bond in order to prepare aminopropanol-introduced HA, and then making the carboxyl group of cinnamic acid and the aminopropanol-derived hydroxyl group in the prepared aminopropanol-introduced HA bind to each other by the ester bond.

The cross-linked HA derivative is a compound in which the photo-reactive HA derivatives as described above are bound to each other by forming a cyclobutane ring in the double bond moiety of the cinnamic acid propyl ester residue existing in such derivative.

The method of forming a cyclobutane ring in the double bond moiety of such cinnamic acid propyl ester residue is not particularly limited, and is, for example, a method of performing light irradiation to a solution of the photo-reactive HA derivative under the conditions in which such cinnamic acid propyl ester residues cause photo-dimerization or photo-polymerization to each other. Regarding the light irradiation, the kind, the wavelength, and the like of light are not particularly limited if the light can cause a photo reaction to the cinnamic acid propyl ester residue without cleavage of the HA glycosidic bond. The light is, for example, the ultraviolet rays having a wavelength of 200 to 400 nm. The intensity of the irradiation light may be suitably selected depending on the properties demanded for the cross-linked HA derivative. The light-illuminating device is preferably an ultraviolet lamp, a high pressure mercury lamp or a metal halide lamp or the like. If necessary, unnecessary wavelength of the light is preferably removed with, for example, a cut filter and the like from the light source.

In regard to the cross-linked HA derivative, it is not necessary that all of the double bond moieties of the cinnamic acid propyl ester residue in the photo-reactive HA derivative are bound to form cyclobutane rings, but only some of the moieties may be bounded to form cyclobutane rings.

Hereinafter, in the cross-linked HA derivative, the ratio (%) of the cinnamic acid propyl ester residues contributing to the formation of the cyclobutane ring structures, to the cinnamic acid propyl ester residues which are present in the photo-reactive HA derivative, is referred to as "a degree of cross-linking". For example, if 20 cinnamic acid propyl ester residues (monomer) are dimerized in the photo-reactive HA derivative into which 100 cinnamic acid propyl ester residues are introduced, 10 dimers are produced, and the degree of cross-linking is 20%.

The degree of cross-linking in the cross-linked HA derivative used in the invention is not particularly limited, but preferably 5% to 40%, more preferably 7% to 35%, and further preferably 10% to 30%.

When the formation of the cyclobutane rings is performed by cross-linking based on the light irradiation, the concentration of the reaction solution in performing the cross-linking is preferably 0.5% to 3.0%, more preferably 0.7% to 2%.

The cross-linked HA derivative may be free, without forming a salt, or may form a pharmaceutically acceptable salt. Examples of the pharmaceutically acceptable salt of the cross-linked HA derivative include sodium salts, potassium salts, magnesium salts, and calcium salts.

<2> The Content of the Cross-Linked HA Derivative of the Invention

The cross-linked HA derivative has a three-dimensional mesh structure. Therefore, a solution in which the cross-linked HA derivative is dissolved in an aqueous medium, has a physical property of hydrogel having viscoelasticity, and particularly, exhibits higher viscoelasticity than solution of sodium hyaluronate prepared in the same concentration exhibits.

The content of the cross-linked HA derivative in the pharmaceutical composition of the invention is preferably 0.5 to 3.0% by weight per volume, more preferably 0.7 to 2.0% by weight per volume, and more preferably 1.0% by weight per volume.

The pharmaceutical composition of the invention may be formulated into various dosage forms, but usually preferably formulated into an injection product which is a liquid formulation for injection.

The content as described above allows the injection of the invention to have suitable fluidity for intra-articular administration using a syringe with an injection needle, and to pass through the injection needle of 18 gauges to 25 gauges. Accordingly, the pharmaceutical composition of the invention is allowed to be used as an intra-articular administration injection product (composition for injection).

<3> Dosage and the Like of the Pharmaceutical Composition of the Invention

The pharmaceutical composition of the invention is administered into the joint, particularly into the knee joint of human. For example, in case of a single administration into the knee joint, the pharmaceutical composition is administered preferably in a dosage of 2 to 5 mL, and more preferably a dosage of 2 to 3 mL. The pharmaceutical composition of the invention may be administered in the same dosage, or nearly the same dosage as the single dosage of the conventional IA-HA products for multiple administrations.

In addition, in regard to the single administration into the knee joint, the dosage (volume of the solution) of the pharmaceutical composition may be further reduced such that the weight of the photo-reactive HA derivative is in the range of 15 to 60 mg, preferably in the range of 25 to 35 mg, and particularly preferably 30 mg per one adult patient (50 to 70 kg).

The pharmaceutical composition of the invention may be administered at an administration interval of 1 week or more, similarly to the conventional IA-HA products. The pharmaceutical composition of the invention has early onset of pain alleviation action, and the effects are durable for a long period, and thus the administration interval can be lengthened compared to the conventional IA-HA products. The pharmaceutical composition of the invention has durable actions up to 13 weeks or more, and more specifically from 13 to 26 weeks. From this, the administration interval can be set to 13 weeks or more, and furthermore in the range of 13 to 26 weeks. The pharmaceutical composition of the invention may be used for durable effects up to at least 13 weeks, and furthermore for durable effects up to 26 weeks. Considering a series of treatments of the current IA-HA products is performed for every 26 weeks, the pharmaceutical composition of the invention can be a continuous type IA-HA product that can be continuously administered by a single administration every 26 weeks.

<4> Coverage and the Like of the Pharmaceutical Composition of the Invention

The pharmaceutical composition of the invention has a pain relief action or pain improvement effect for human joint disease. The pharmaceutical composition of the invention has early onset of therapeutic effects after administration. That begins to show nearly maximum effects in the period between 1 week and 3 weeks after the administration, and the effects are durable for 13 weeks or more, and furthermore for 26 weeks. This "therapeutic effect" is not particularly limited as long as it is an effect of improving symptoms of a human joint disease, but includes an effect of improving physical function, an effect of improving stiffness, an effect of relieving pain, and the like as examples thereof, and is preferably an effect of relieving pain.

The pharmaceutical composition of the invention has onset of such improvement effects between 1 week and 3 weeks after a single administration, and is characteristically durable for an ultralong period such as least 13 weeks, and furthermore 26 weeks.

The pharmaceutical composition of the invention may include additives such as a solvent, a pH regulator, a tonicity agent and a stabilizer, which are used in usual preparation of products for injection, if necessary unless they cause loss of desired effects, and cause side-effects. For example, examples of the solvent for the cross-linked HA derivative include water for injection, physiological saline, and phosphate buffer saline. Further, examples of the additives also include sodium dihydrogen phosphate, sodium hydrogen phosphate, and sodium chloride, which are used as a pH regulator or a tonicity agent in the preparation of a usual injection product.

In addition, the pharmaceutical composition of the invention achieves early onset of prominent therapeutic effects after a single administration. As shown in Examples described below, particularly regarding the pain-relieving effects, about 90% or more of the maximum therapeutic effects are achieved at 3 weeks after the administration of the pharmaceutical composition of the invention. Such rapid-onset and prominence of the pharmaceutical composition of the invention are not found with conventional IA-HA products, and thus it is also considered that the active ingredient of the invention has a potential to have different mechanisms from those of the conventional IA-HA products, whereby to have actions such as rapid-acting analgesic action. In other words, it has been found for the first time in the invention that the cross-linked HA derivative of the invention has a potential to have different mechanisms from those of the hyaluronic acid component in the conventional IA-HA products in pain improvement action.

In addition, as shown in Examples described below, a group to whom the pharmaceutical composition of the invention is administered, had significantly fewer patients who experienced pain again to be required retreatment at 26 weeks after an initial single administration compared to the PBS-administered group. This results the administration of the pharmaceutical composition of the invention had prominently delayed recurrence of pain.

For reference, ARTZ (registered trademark, manufactured by SEIKAGAKU Corporation), which is one of commercially available IA-HA products, is an intra-articular injection fluid with a volume of 2.5 mL per one ampule or one syringe, and a basic prescription thereof is one ampule or one syringe per single administration per week 5 times continuously. Consequently, the dose of ARTZ used in the single treatment course is 12.5 mL. In addition, Synvisc-One (trademark, manufactured by Genzyme Co.) is used as 6 mL single administration in a single injection as a prescription thereof.

Overall, the pharmaceutical composition of the invention is based on three main merits: single administration; small dosage; and long therapeutic effects, and may be also used, for example, as a formulation for a single administration every 3 months to a half year for a chronic joint disease. Needless to say, the pharmaceutical composition of the invention may be also used as a formulation that is administered at an interval of 6 months or more in consideration of the durability of the improvement effects in patients and patients' condition in symptom level and the like. As a matter of course, only a single administration, i.e., only a single treatment is also possible.

Hereinafter, the present invention will be further explained with reference to Examples, but the technical scope of the invention is not limited thereto.

PREPARATION EXAMPLE

Preparation of Cross-Linked HA Derivative

According to the method described in International Publication Pamphlet WO 2008/069348 other than using sodium hyaluronate having a weight average molecular weight of 900000 to 1000000 and cinnamic acid 3-aminopropyl hydrochloride as raw materials, a cross-linked hyaluronic acid derivative having 10% to 25% of a degree of substitution and 10% to 30% of a degree of cross-linking was appropriately prepared and a solution of the cross-linked hyaluronic acid derivative having a concentration of 1.0% by weight per volume was prepared This solution is referred to as "test substance" below.

EXAMPLE 1

Study Methods

A multi-center, double-blind, parallel-group controlled study was conducted for patients with knee osteoarthritis, and effectiveness of a single injection of the cross-linked HA derivative of the invention was verified. Phosphate buffered saline (PBS) solution was used as a placebo control.

The screening of patients was performed based on the inclusion criteria and the exclusion criteria described below before 1 to 2 weeks of the administration of the test substance. Patients who met the criteria were randomized to a group to whom the cross-linked HA derivative of the invention was administered, or a group to whom the PBS was administered. The cross-linked HA derivative group had 249 patients, and the PBS group had 128 patients (a total of 377 patients).

To each of the patients in the cross-linked HA derivative administration group of the invention, the test substance was single injected intra-articularly into the one affected knee in the dosage of 3 mL/joint. To each of the patients in the PBS administration group, PBS was single injected in the same manner. Physicians who performed the administration examined the affected knee of the patients and aspirated the fluid in the joint if the effusion presented prior to the administration.

The improvement effects were assessed based on the assessment method described below at the time points of Week 1, Week 3, Week 6, Week 9 and Week 13, respectively after the injection.

In addition, acetaminophen as a rescue medication was distributed on each assessment day, and the patients were allowed to take up to 4000 mg acetaminophen per day. In addition to acetaminophen, the patients were allowed to take non-steroidal anti-inflammatory analgesic drugs, over-the-counter drugs (OTC), herbal product and chondroprotective agents during the study period only if the patients had continued to take such drugs at a stable dose for more than four weeks before administration of the test substance. In addition, intermittent use of opioid analgesic drugs were also allowed during the study. However, for 24 hours before each assessment day, any concomitant therapy was prohibited.

[Inclusion Criteria and Exclusion Criteria]
(1) Inclusion Criteria

Patients who meet all of the following criteria can be qualified for this study except those met any one of the exclusion criteria described below.

Patients between the ages of 40 and 80 years, who have a symptom of osteoarthritis of the knee.

Patients who have knee pain while standing or walking at least 4 weeks in duration.

Patients who have Kellgren-Larence grade 1 to 3 by X-ray.

Patients who have Western Ontario and McMaster Universities Osteoarthritis Index (WOMAC (registered trademark)) pain subscore≥40 mm in the affected knee and 20 mm in the contralateral knee. Herein, WOMAC (registered trademark) was measured by a 100 mm. Visual analog scale (VAS).

Patients who have willingness to discontinue current OA treatment other than allowed concomitant therapies.

(2) Exclusion Criteria

Patients who have Kellgren-Larence grade 4 by X-ray.

Patients who have inflammatory diseases of knee in the affected other than OA; patients who have severe knee joint effusion; or patients who have severe false alignment of the axis of the knee.

Patients who have history of joint replacement of knee or hip; patients who had knee joint surgery within previous 12 months; patients who had arthroscopy within 3 months; or patients who had intra-articular administration of a hyaluronic acid product within previous 6 weeks.

Patients who have serious systematic arthropaties/infectious skin disease in the affected knee for assessment.

[Assessment Method]

Effectiveness of the cross-linked HA derivative was assessed by using WOMAC scoring (The Journal of Rheumatology 1988; 15:12, p. 1833-1840) developed by Dr. Nicholas Bellamy. Herein, WOMAC is a registered trademark. Hereinafter, indication of this registered trademark will be omitted.

The WOMAC scoring used herein is a method in which patients are questioned for total 24 items (Total) composed of 3 parts: Pain, Stiffness and Physical function, and they are scored based on the answers.

In this study, the primary measurement was WOMAC pain subscore, and the secondary measurements were WOMAC stiffness subscore, WOMAC Physical function subscore, and Total WOMAC score.

The WOMAC scoring is patient's reported outcome, which is established as the assessment method of OA, which is composed of total 24 questions about Pain, Physical function and Stiffness as described above. The answering method to the questions includes 2 kinds: VAS (Visual Analog Scale) and Likert scale. VAS is a method in which patients indicate degrees of their own feelings for each question on a 100 mm line and the degree is determined by the position. The position may be represented by a distance from the left end on the scale. On the other hand, Likert Scale is a method in which patients indicate degrees of their own feelings for each questions by 5 categorical scales. In this study, VAS is used in the assessment of the degrees of the pain, the physical function and the stiffness of patients.

For example, patients are asked the same questions related to pain in each assessment before and after administration, and the patients answer by indicating the position (degree) in the scale. Based on the difference between the distance indicated by patient before the administration (pre-administration reference value (Baseline)) and the distance indicated by patient in each assessment after the administration, the improvement effects are converted to numeral values.

The WOMAC score is widely used as an index of OA therapeutic effects, and the reliability and responsibility of WOMAC score on OA therapeutic effects has been also validated (The Journal of Rheumatology 2000; 27: 11, p. 2635-2641).

Effectiveness analyses were conducted using intention-to-treat population (ITT population) and per protocol population (PP population). The ITT population had a total of 375 patients in which 247 patients administered the cross-linked HA derivative of the invention and 128 patients administered the PBS. Two patients who did not have any post-injection visit were excluded.

The PP population had a total of 344 patients in which 229 patients administered the cross-linked HA derivative of the invention, and 115 patients administered the PBS. Patients who violated the protocol of this study were excluded.

[Results]

Results of the PP population analysis for WOMAC pain subscore are shown in Table 1, and results of the ITT population analysis are shown in Table 2.

TABLE 1

|  | Week 1 | Week 3 | Week 6 | Week 9 | Week 13 |
| --- | --- | --- | --- | --- | --- |
| Mean value of cross-linked HA derivative (standard deviation) | 20.8 mm (24.50) | 28.9 mm (25.52) | 31.7 mm (28.00) | 31.7 mm (28.47) | 27.8 mm (29.84) |
| Mean value of PBS (standard deviation) | 19.1 mm (24.71) | 20.9 mm (24.50) | 23.4 mm (26.64) | 25.7 mm (25.93) | 20.5 mm (28.66) |

TABLE 2

|  | Week 1 | Week 3 | Week 6 | Week 9 | Week 13 |
| --- | --- | --- | --- | --- | --- |
| Mean value of cross-linked HA derivative (standard deviation) | 20.7 mm (24.09) | 28.7 mm (25.23) | 31.2 mm (27.61) | 31.7 mm (27.91) | 27.8 mm (29.26) |
| Mean value of PBS (standard deviation) | 19.8 mm (24.61) | 21.3 mm (25.00) | 24.7 mm (27.31) | 27.4 mm (26.46) | 22.6 mm (29.31) |

The cross-linked HA derivative group of the invention showed statistically significant improvement at the time point of Week 3 after the administration over the PBS group, and also lasted its effects after Week 3. The PP population showed statistically significant difference over the PBS group with a p-value of 0.05 or less at the time points of Week 3, Week 6 and Week 13. These analyses showed advantage for the cross-linked HA derivative group of the invention though there was no significant difference at Week 9.

In addition, a figure representing the results of the model-estimated regression analysis in the ITT population is shown in FIG. 1. In analyses of pain improvement for 13 weeks after the administration, the cross-linked HA derivative administration group improved pain statistical significantly over the PBS administration group through Week 1 to Week 13 and through Week 3 to Week 13. The p-value between Week 1 and Week 13 after the administration was 0.0483, and the p-value between Week 3 and Week 13 after the administration was 0.0495, both of which showed statistically significance over the PBS group.

Furthermore, the improvements of each WOMAC score at the time point of Week 13 by the regression model were analyzed using the PP population. The results are shown in Table 3. The cross-linked HA derivative group showed statistically significant improvement in WOMAC pain subscore over the PBS group at the time point of Week 13 after the administration. The cross-linked HA derivative group showed statistically significant improvement both in Total WOMAC score and WOMAC Physical function subscore, which are secondary measurements for effectiveness, and showed statistically significant difference over the PBS group. Although there was no statistically significant difference, WOMAC stiffness subscore showed favor trend in the cross-linked HA derivative group.

The Estimated difference below is the difference calculated using the regression model.

TABLE 3

|  | Estimated difference | 95% Confidence Interval (CI) Lower value, Upper value | p-value |
| --- | --- | --- | --- |
| WOMAC Pain Subscore | 7.41 | 0.54, 14.28 | 0.035 |
| Total WOMAC Score | 7.27 | 0.60, 13.95 | 0.033 |
| WOMAC Physical function Subscore | 7.30 | 0.54, 14.05 | 0.035 |
| WOMAC Stiffness Subscore | 6.82 | −0.22, 13.86 | 0.058 |

In addition, Strict OMERACT-OARSI Response was analyzed to verify the clinical usefulness. Statistically significant improvement was demonstrated for the cross-linked HA derivative group (see Table 4).

Strict OMERACT-OARSI Response defines patients who reported not less than 50% and at least 20 mm of improvement from baseline in WOMAC pain subscore or WOMAC Physical function subscore, as a high responder. The total of these responder groups is referred to as the Strict OMERACT-OARSI responder.

TABLE 4

|  | Odds ratio | p-value |
|---|---|---|
| Strict OMERACT-OARSI | 1.74 | 0.012 |

In addition, regarding the early onset of the improvement effect, the mean improvement from the baseline for WOMAC pain subscore, Total WOMAC score, WOMAC Physical function subscore and WOMAC stiffness subscore at Week 3 was compared between the cross-linked HA derivative group and the PBS group. The WOMAC pain subscore showed the improvement effect exceeding 90% of the maximum improvement effect at Week 3, and the p-value that represents the statistical significance of the cross-linked HA derivative group to the PBS group is estimated (Table 5). The p-value was less than 0.05 (p<0.05) in any other assessments, which showed statistically significant difference.

TABLE 5

|  | P-value at Week 3 |
|---|---|
| WOMAC Pain Subscore | 0.0065 |
| Total WOMAC score | 0.0129 |
| WOMAC Physical function Subscore | 0.0205 |
| WOMAC Stiffness Subscore | 0.0336 |

Furthermore, after completion of the 13 week observation with respect to the administration of the cross-linked HA derivative or PBS, observation was extended for further 13 weeks, to assess effectiveness of the cross-linked HA derivative group up to 26 weeks from the initial administration.

WOMAC pain subscore was assessed at Weeks 16, 19, 22 and 26 from the first administration, and patients who did not meet the criteria below were chosen as the effectiveness-durable group with first administration, and the survival analysis was performed using Cox-hazard model for each treatment group.

Endpoint A: ≥40 mm in WOMAC pain subscore.
Endpoint B: ≥40 mm in WOMAC pain subscore, and improvement<20 mm from baseline of the first administration.

Cox-hazard analysis showed effectiveness for the cross-linked HA derivative administration group in both Endpoints up to 26 weeks (Endpoint A: p=0.019, Endpoint B: p=0.027).

CONCLUSION

It was found that single injection of the cross-linked HA derivative showed durable improvement effects up to at least 26 weeks from the injection.

The cross-linked HA derivative showed prominent improvement not only in the pain subscore, but also in the physical function subscore and other scores compared to PBS group, and thus demonstrated multi-dimentional effectiveness in a knee OA.

In addition, the cross-linked HA derivative showed the rapid-onset of the pain improvement at 3 weeks after the injection, and also showed statistically significant difference compared with the PBS.

Furthermore, the cross-linked HA derivative showed significant improvement effects up to 13 weeks, and furthermore up to 26 weeks. In addition, the cross-linked HA derivative group had no statistically significant difference from the PBS group in the expression rate of adverse events, and had no severe side-effect. These demonstrated high safety as an intra-articular injection of the cross-linked HA derivative.]

INDUSTRIAL APPLICABILITY

The present invention provides a new agent for relieving pain in a joint disease that shows early onset of pain-relieving effects after administration, and has long term durability up to 13 week or up to 26 weeks, and is a continuous type therapeutic agent for joint diseases that greatly reduces a burden to patients, and thus has applicability in the industry such as medical industry.

The invention claimed is:

1. A method for relieving pain in a joint disease, comprising:
   administering to a human subject in need thereof a pharmaceutical composition comprising hyaluronic acid that is cross-linked by cyclizing a double bond in a moiety of a cinnamic acid in a partially amidated hyaluronic acid represented by Formula (1), to form a cyclobutane ring, $$[Ar-CH=CH-COO-(CH2)n-NH-]m-HA \quad (1)$$

in which Ar represents an optionally substituted phenyl group, n represents an integer of 2 or 3, HA represents a carboxy residue of the hyaluronic acid, and m represents an amidation ratio of the hyaluronic acid to a total of a carboxyl group and is 3% to 50% relative to the total carboxyl group; and
   a pharmaceutically acceptable carrier,
   wherein the pharmaceutical composition is an injection product,
   wherein the cross-linked hyaluronic acid is 1% by weight per volume of the injection product,
   wherein a single dosage of the injection product is 2 to 3 mL, and
   wherein the pharmaceutical composition is a single-dose preparation that is administered at an interval of 13 weeks or more.

2. The method of claim 1 wherein the pharmaceutical composition is used for durable effects up to at least 13 weeks.

3. The method of claim 2 wherein the pharmaceutical composition is used for durable effects up to at least 26 weeks.

4. The method of claim 1 wherein the subject suffers from a joint disease.

5. The method of claim 1 wherein the subject suffers from pain from a joint disease.

6. The method of claim 1 wherein the subject suffers from osteoarthritis of the knee.

* * * * *